United States Patent [19]

Krezanoski

[11] 4,031,209

[45] * June 21, 1977

[54] AQUEOUS SOLUTION SUITABLE FOR DISSIPATING AVAILABLE IODINE CONTAINED IN AN IODOPHOR

[75] Inventor: Joseph Zenon Krezanoski, Los Altos, Calif.

[73] Assignee: Flow Pharmaceuticals, Inc., Palo Alto, Calif.

[ * ] Notice: The portion of the term of this patent subsequent to Oct. 7, 1992, has been disclaimed.

[22] Filed: June 2, 1975

[21] Appl. No.: 582,762

Related U.S. Application Data

[63] Continuation-in-part of Ser. No. 315,793, Dec. 18, 1972, Pat. No. 3,911,107.

[52] U.S. Cl. .............................. 424/150; 424/317; 424/319; 424/365
[51] Int. Cl.$^2$ ................. A01N 11/00; A61K 33/18
[58] Field of Search ................... 424/150, 317, 365

[56] References Cited

UNITED STATES PATENTS

| | | | |
|---|---|---|---|
| 2,698,819 | 1/1955 | Ziemcak | 424/150 |
| 3,028,299 | 4/1962 | Wincov et al. | 424/150 |
| 3,028,300 | 4/1962 | Cantor et al. | 424/274 |
| 3,132,068 | 5/1964 | Behrman | 424/150 |
| 3,285,816 | 11/1966 | Kaplan et al. | 424/150 |
| 3,438,906 | 4/1969 | Duvall | 424/150 |
| 3,911,107 | 10/1975 | Krezanoski | 424/78 |
| 3,954,644 | 5/1976 | Krezanoski et al. | 252/106 |

OTHER PUBLICATIONS

Acta Polon. Pharma., vol. 20, No. 6, pp. 455–457 (1963).
Klin. Oczna, 36(1), pp. 27–32 (1966) (Ref. R & S cited in copending Ser. No. 315,793, U.S. 3,911,107).
Chemical Abstracts, 66:4545t (1967).
Chemical Abstracts, 75:52752q. (1971).
Merck Index Ed. 8, p. 971 (1968).
Chemical Abstracts, 55:1802i (1961).
Iodinol Med. Vet. Eksp. Klin. Issled. Akad. Nauk. S.S.S.R. Bot. Inst., 1967, pp. 5–20.
Chemical Abstracts 57:966b (1962).

*Primary Examiner*—Leonard Schenkman
*Attorney, Agent, or Firm*—Finnegan, Henderson, Farabow & Garrett

[57] ABSTRACT

An aqueous solution suitable for dissipating, at a controlled rate, available iodine contained in an iodophor is disclosed. The aqueous dissipating solution contains sorbic acid or soluble salts thereof and ethylenediaminetetraacetic acid or soluble salts thereof. Preferably, the dissipating solution also contains an ammonium, alkali metal, or alkaline earth metal salt of a boron oxyacid. Also disclosed are techniques for sterilizing contact lenses and sterile solutions, suitable for maintaining sterility of a previously sterilized object, comprising admixtures of the dissipating solutions with iodophor solutions.

19 Claims, No Drawings

AQUEOUS SOLUTION SUITABLE FOR DISSIPATING AVAILABLE IODINE CONTAINED IN AN IODOPHOR

CROSS-REFERENCES TO RELATED APPLICATIONS

This application is a continuation-in-part of copending U.S. application Ser. No. 315,793, filed Dec. 18, 1972, now U.S. Pat. No. 3,911,107.

Field of the Invention

The present invention pertains to an aqueous solution suitable for dissipating, at a controlled rate, available iodine contained in an iodophor. The present invention also pertains to techniques and aqueous, antiseptic solutions particularly useful for sterilizing and disinfecting soft contact lenses. The antiseptic solutions preferably comprise an admixture of the dissipating solution and an aqueous iodophor solution containing polyvinyl alcohol, iodine and water soluble iodide salts.

BACKGROUND OF THE INVENTION

The use of iodine as a germicidal agent is well known. Iodine as such or in various molecular combinations has been used medicinally since soon after its discovery. Iodine was used to treat battle wounds as early as 1839. In various forms, iodine is an outstanding germicide for the skin, for wounds both internal and external, and for sterilization purposes including such things as surgical instruments. It has also been used to disinfect drinking water, swimming pools, and the like, and to sanitize utensils and other objects which might come in contact with organic material subject to decay and bacterial attack.

Iodine is an outstanding therapeutic agent which is useful against a great variety of organisms including viruses, bacteria, spores, yeast, molds, protozoa, fungi, worms, nematodes, and the like. In addition, iodine has a relatively low tissue toxicity. The relatively low toxicity is due to the breakdown of iodine to the iodide ion ($I_2 \rightarrow I-$); the iodide ion is non-toxic.

Iodine, however, does have some serious drawbacks. It is a strong primary irritant and a sensitizer. Furthermore, while it destroys bacterial protein, it also, to some extent, destroys animal protein as well. Additionally, iodine has undesirable odor and staining properties.

It has been discovered that certain compounds act as carriers or "taming" agents for iodine. The term "iodophor" is used to refer to any product in which surface active agents act as carriers and solubilizing agents for iodine. Known carriers include a variety of high molecular weight materials such as starch and various synthetic polymers. Typical synthetic polymers are exemplified by polymeric vinyl lactams and high molecular weight oxyalkaline derivatives of reactive hydrogen compounds generally characterized as the alkaline oxide condensates having surface active properties. Specific examples of suitable polymeric material include polyvinyl pyrrolidone, polyvinyl oxizolidone, polyvinyl imidazole, polyvinyl morpholone, polyvinyl caprolactam, polyvinyl alcohol, and ethylene and propylene oxide condensates with alcohols, amides and phenols.

Iodophors generally enhance the bactericidal activity of the iodine while reducing vapor pressure and odor. In addition, iodophors decrease staining properties and permit wide dilutions with water. Additionally, the irritant properties of iodine are markedly reduced when employed in the form of an iodophor.

A particularly useful iodophor composition results from the interaction between iodine, potassium iodide, and polyvinyl alcohol in a water solution. Such a composition is disclosed in Mokhnach, "Iodine-High Polymers and Their Use in Medicine and Veterinary Medicine", (Boton. Inst. im. Komarova, Leningrad) *Iodinol Med. Vet. Eksp. Klin. Issled. Akad. Nauk S.S.S.R. Bot. Inst.*, 1967, 5–20 (Russ.). This composition has been used to treat purulent surgical diseases, varicose ulcers, thermic and chemical burns, and in veterinary practice to treat a wide variety of diseases in animals. It is an effective antiseptic, equally effective with respect to gram positive and gram negative microflora, viruses and fungi. The chemotherapeutical index, i.e., ratio of maximum endurable dose to the medicinal dose of this composition is very large. While these iodophors are very effective, they are not as stable as is desired, i.e., they have a somewhat limited shelf life.

Copending U.S. Application Ser. No. 315,793, Dec. 18, 1972, now U.S. Pat. No. 3,911,107, discloses aqueous solutions prepared from iodine, a water soluble iodide salt, boric acid, and polyvinyl alcohol, which are particularly useful in connection with the present invention. The iodophors of the copending application have a long shelf life coupled with a broad range of germicidal, fungicidal, virucidal, and sanitizing properties. These iodophor solutions, which may be in the form of concentrates or dilute free iodine releasing solutions, may be used for cleaning, sanitizing and disinfecting inanimate as well as animate objects.

For many uses, controlled dissipation of the available iodide in iodophor solutions is not a prerequisite for achieving sterility, tissue tolerance, and ultimate safety. However, there are instances where total destruction of the available iodine ($I_2$) is desirable either while the iodophor is acting or after the iodophor has acted.

Basically, all compounds commonly known as antioxidants having the appropriate redox potential to convert $I_2$ to $2I-$ could be used to destroy available iodine. Examples of such compounds would include alcohols, aldehydes, alkenes, alkynes, aromatic hydrocarbons, amides, quinones, hydroxy acids, sugars, amino acids, sulfites, thiosulfates, sulfhydryl containing compounds, and polyunsaturated organics.

Solutions of such compounds have been found to destroy all of the available iodine at different rates. Many such compounds will be satisfactory for various industrial purposes. However, safety and tissue tolerance requirements restrict the number of compounds suitable for human and animal use.

Compounds suitable for human and animal use include sodium sulfite, sodium thiosulfate, sodium hydrogen sulfite, cysteine, methionine, ascorbic acid, sorbic acid and disodium edetate. Almost immediate inactivation of available iodine in iodophors takes place upon treatment with greater than molar equivalents of inorganic sulfites and thiosulfates, methionine, cysteine and ascorbic acid. This virtually instant neutralization may be desirable in some instances. Where maintenance of sterility of the treatment system is not required, neturalization can be accomplished quite readily with such compounds.

In other instances, a slow but predictable rate of iodine dissipation is more desirable. Additionally, maintenance of sterility after treatment may be required with certain prostheses, e.g., contact lenses stored in a storage case. Under such circumstances, it is necessary that the iodine dissipating solution be sterile and have resterilizing capability as well. Thus, an ideal iodine dissipating agent must be able to not only dissipate iodine, but also must act as an anti-microbial preservative, and have good tissue tolerance properties.

The aqueous solutions of the present invention are extremely well suited for dissipating, at a controlled rate, available iodine contained in iodophor solutions. The solutions are sterile, possess good tissue tolerance properties, and act as an anti-microbial preservative. In addition, the solutions of the present invention are useful as contact lens rinsing and boiling solutions and as eye irrigating solutions.

The aqueous solutions of the present invention are particularly useful in connection with techniques for sterilizing prosthetic and diagnostic devices, particularly contact lenses. Admixtures of the dissipating solution of the present invention with an iodophor solution provide solutions which are effective to maintain the sterility of the treated devices over extended periods of time.

SUMMARY OF THE INVENTION

The present invention pertains to sterile aqueous solutions comprising:
a. from about 0.01% to about 5.0% by weight sorbic acid or a soluble salt thereof; and
b. from about 0.01% to about 5.0% by weight ethylenediaminetetraacetic acid or a soluble salt thereof.

The remainder of the composition may comprise solely water of may include various other ingredients which will impart special properties. For example, various alkali metals and alkaline earth metal salts of mineral acids may be added to the composition to adjust osmotic properties (tonicities) of the solutions to make them better tolerated by living tissue.

Preferably, the solutions of the present invention contain from about 0.1% to about 2.0% of an ammonium, alkali metal or alkaline earth metal salt of a boron oxyacid. Inclusion of a boron oxyacid salt imparts enhanced stability to sterile solutions comprising an admixture of the aqueous solutions of the present invention with iodophor solutions.

The aqueous solutions of the present invention, which possess anti-microbial activity, may be used as contact lens rinsing and boiling solutions or as eye irrigating solutions. However, they are particularly well suited for dissipating, at a controlled rate, the available iodine contained in an iodophor.

The present invention also pertains to methods of sterilizing and disinfecting contact lenses with iodophor solutions. Contact lenses, in particular soft hydrophilic gel lenses, may be sterilized by contacting with an iodophor solution. Subsequently, the available iodine contained in the iodohpor is dissipated, preferably by the addition of the aqueous solutions of the present invention.

An admixture of the preferred aqueous solutions of the present invention with an iodophor provides a stable solution effective to maintain the sterility of a previously sterilized device. Preferably, the iodophor employed in connection with the present invention comprises from about 0.00005% to about 10.0% by weight iodine, from about 0.0001% to about 20.0% by weight of a water soluble iodide salt, and from about 0.001% to about 25.0% by weight polyvinyl alcohol.

DESCRIPTION OF THE EMBODIMENTS

The sterile aqueous solutions of the present invention contain sorbic acid, or a soluble salt thereof, and ethylenediaminetetraacetic acid, or a soluble salt thereof. Such solutions dissipate available iodine in iodophor compositions at a controlled rate, present no serious tissue tolerance problems, and may be sterilized to a preserved solution.

The mechanism for dissipating available iodine by the novel dissipating solution of the present invention is not understood. The sorbic acid or its water soluble salts and ethylenediaminetetraacetic acid or its water soluble salts in an aqueous vehicle can destroy iodine at a predetermined rate ranging from 1 to 300 min. depending upon the concentration of iodine in the iodophor solution; the amount added to the dissipating solution; the concentration of the two ingredients in the dissipating solution; pH; and temperature.

The dissipating solution can be conveniently used over a pH range of about 2 to 10; the higher the pH, the more rapid the dissipation of the available iodine. Preferably, the pH is adjusted to approximately 7.0 by adding a base such as NaOH. Increases in temperature above room temperature also increases the dissipation rate. The dissipating solution may conveniently be employed in amounts of from 1 to 1000 parts by weight per part by weight of available iodine in the iodophor.

Preferably, the dissipating solutions of the present invention contain from about 0.1% to 2.0% of an ammonium, alkali metal, or alkaline earth metal salt of a boron oxyacid. Suitable salts include those of boric acid ($H_3BO_3$), metaboric acid ($HBO_2$), and pyroboric acid ($H_2B_4O_7$). Specific examples of suitable salts include borax ($Na_2B_4O_7.10H_2O$), sodium tetraborate ($Na_2B_4O_7$), sodium tetraborate pentahydrate ($Na_2B_4O_7.5H_2O$), sodium metaborate ($NaBO_2.4H_2O$), potassium metaborate ($KBO_2$), potassium tetraborate ($K_2B_4O_7.5H_2O$), lithium metaborate dihydrate ($LiBO_2.2H_2O$), lithium tetraborate ($Li_2B_4O_7.5H_2O$), calcium metaborate [$Ca(BO_2)_2$] and hydrates thereof, calcium tetraborate ($CaB_4O_7$), magnesium orthoborate ($3MgO.B_2O_3$), magnesium metaborate [$Mg(BO_2)_2.8H_2O$], magnesium pyroborate ($Mg_2B_2O_5.H_2O$), lithium metaborate ($LiBO_2.8H_2O$), lithium tetraborate ($Li_2B_4O_7.5H_2O$), ammonium tetraborate [$(NH_4)_2B_4O_7.4H_2O$] and ammonium pentaborate [$(NH_4)_2B_{10}O_{16}.8H_2O$]. Sodium borates are preferred. It will be appreciated, of course, that the hydrates referred to above are not present in solution as hydrates.

It is often desirable to add up to about 2.0% of a water soluble alkali metal or alkaline earth metal salt of a mineral acid to the dissipating solutions of the present invention. The salts may be added to adjust osmotic properties (tonicities) of the solutions to make them better tolerated by living tissues. Salts of hydrochloric, sulfuric, nitric, and phosphoric acids are suitable, including NaCl, KCl, $CaCl_2$, $MgCl_2$, and corresponding phosphate, nitrate and sulfate salts.

The dissipating solutions of the present invention are suitable for use with a wide range of iodophors. Typical examples of commercially available iodophors which may be treated with the dissipating solutions of the present invention to achieve a controlled, dissipating action include: polyvinylpyrrolidone-iodine; nonylphenolethoxylate-iodine; soluble starch-iodine; betacyclodextrin-iodine; polyoxyethylene-polyoxypropylene condensate-iodine; ethoxylated linear alcohol-iodine, etc.

The iodophor solutions disclosed in copending application Ser. No. 315,793 now U.S. Pat. No. 3,911,107 are particularly well suited for use with the dissipating solutions of the present invention. These iodophors comprise an aqueous antiseptic solution containing:
a. from about 0.00005% to about 10% by weight iodine;
b. from about 0.0001% to about 20% by weight of a water soluble iodide salt;
c. from about 0.001% to about 25% by weight polyvinyl alcohol; and
d. from about 0.001% to about 10% by weight boric acid.

The iodophor solutions disclosed in copending application Ser. No. 315,793 has shown to have a broad range of germicidal, fungicidal, virucidal, and sanitizing properties, coupled with a high degree of stability. However, it has been found that such solutions have greater strength, i.e., greater germicidal, fungicidal, virucidal, and sanitizing characteristics, at some loss in stability, if the boric acid is omitted from the solutions.

Accordingly, the dissipating solutions of the present invention are preferably used in connection with iodophors which do not contain boric acid. When boric acid is omitted from the iodophor solutions, the iodophors are advantageously employed with the preferred, i.e., boron oxyacid salt containing, dissipating solutions of the present invention. The presence of such a salt results, when the dissipating solution is combined with the iodophor, in a stable solution suitable for maintaining sterility of previously sterilized objects.

The preferred iodophors for use with the present invention may contain from about 0.00005% to about 10%, and more preferably about 0.002% to about 5% by weight iodine. The solutions may be prepared in the form of concentrates and subsequently diluted to the concentration desired for a particular use (typically 5 to 100 ppm available iodine). Dilution can be achieved with purified water or with the disclosed dissipating solution.

The iodophor compositions, in dilutions of up to 1:200,000 available iodine, will destroy all vegetative forms of bacteria in 15 minutes. Even in such dilutions, the solutions provide a color indication of antimicrobial activity. If there is no color, there is no germicidal activity.

Preferably, the aqueous antiseptic iodophor solutions also include about 0.0001% to about 20%, and more preferably about 0.004% to about 10% by weight, of a water soluble iodide salt. Potassium iodide is preferred, but any of the well-known soluble salts of iodine, such as sodium iodide or hydriotic acid may also be employed. The iodide salt aids in the initial solubilization of the iodine and simplifies the manufacture of the final solutions.

In solution, the water soluble iodide salt results in the formation of the negative iodide ion. This ion reacts with the iodine in accordance with the well-known reaction: $I_2 + I^- \rightarrow I_3^-$. The resultant triiodide ion is water soluble and yields free iodine in the use applications of the solutions of the present invention. It is not known whether the boric acid and polyvinyl alcohol form complexes with $I_2$ or $I_3^-$.

A wide variety of polyvinyl alcohols in amounts from about 0.001% to about 25%, and preferably from about 0.1% to about 20% by weight, may be used in the iodophor compositions. Various grades of polyvinyl alcohol are available commercially from a number of sources. Examples of these include Elvanol (E.I. DuPont de Nemours and Co., Inc., Wilmington, Delaware) and Vinol (Colton Chemical Co., Cleveland, Ohio). Polyvinyl alcohols are synthetic water soluble resins derived through controlled polymerization of vinyl acetate and partial or complete hydrolysis of the polyvinyl alcohol.

By varying the degree of polymerization and the extent to which the acetate groups and the polymer chain are hydrolyzed, a versatile series of resins useful in iodophor compositions may be obtained. Solution viscosity increases with increasing degrees of polymerization; accordingly, one may choose the grade of polyvinyl alcohol best suited for a particular use from a rather wide resin series. The same degree of flexibility exists with respect to the degree of polyvinyl acetate hydrolysis. Ethanol, for example, is availabile in grades which produce 4.0% solutions having viscosity range of 1.8 – 135 cp at 20° C and a percentage hydrolysis ranging from 85 – 100%.

The polyvinyl alcohols, when dissolved in water, yield solutions having a pH within the range of 5 – 8; maximum stability is obtained with acid pH. Depending on the concentration and particular polyvinyl alcohol employed, the viscosities of the iodophor solutions may be varied in the range of from 1.1 to 10,000 cp at 20° C.

Polyvinyl alcohols may be depicted as follows:

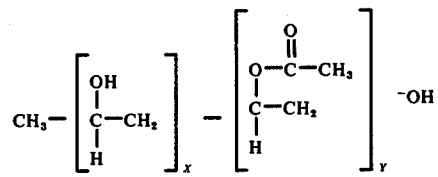

The "X" and "Y" refer, respectively, to the relative number of free hydroxyl and acetylated groups in the resin chain. Polymers which are completely hydrolyzed to polymers containing about 25.0% acetate groups are suitable in the compositions of the present invention.

A particularly suitable polyvinyl alcohol is that sold under the trade name of Elvanol 5105. This particular grade of polyvinyl alcohol is from 88.0% to 90.0% hydrolyzed and has a volatile content of up to 5.0%. A 4.0% solution of this material in water has a viscosity of 5 cp at 20° C.

To enhance stability, it is desirable to adjust the hydrogen ion concentration of the iodophor solutions into the pH range of about 3 to 8 and preferably, 3.5 to 7.0. Any poorly oxidizable acid may be used to adjust the pH; examples of suitable acids include $H_3PO_4$, HCl, acetic acid, $H_2SO_4$, nitric acid, etc.

In certain applications, it is desirable to adjust the osmotic properties of the iodophor solution. Tonicities equivalent of a 0.1% to a 5.0% aqueous sodium chloride solution are desirable to make the aqueous antiseptic iodophor solution of the present invention better tolerated by living tissues. Osmotic properties may be adjusted by adding appropriate amounts of alkali metal and alkaline earth metal salts. Specific examples of suitable salts include NaCl, KCl, $CaCl_2$, $MgCl_2$ and corresponding phosphate, nitrate and sulfate salts.

The wetting and cleaning properties of the antiseptic iodophor solution can be enhanced by the addition of conventional neutral anionic, cationic, and nonionic detergents. Numerous examples of suitable detergents are well known in the art. Detergents may conveniently be included in the solution in amounts up to 25.0% by weight.

It is recognized, of course, that the iodophor solutions of the present invention do not contain the various recited ingredients as such. In the solution, the iodine forms complexes with the polyvinyl alcohol and the various compounds, such as the water soluble salts, which will at least to some extent ionize.

Iodine availability and stability in the iodophor solutions may be determined by direct titration with standardized sodium thiosulfate solutions. This classic oxidation-reduction type reaction is well known to those skilled in the art of iodine chemistry.

The aqueous antiseptic iodophor solution, which may range in composition from concentrates to dilute free iodine releasing products, are useful for cleaning, sanitizing, and disinfecting inanimate as well as animate objects. The composition may be marketed as dilute iodine yielding solutions ready for use or as concentrates which may be diluted according to need prior to use.

The dissipating compositions of the present invention, in combination with iodophor solutions, are particularly suitable for sterilizing contact lenses of all types, prior to application to the cornea. Hydrophilic gel (soft) lenses which are now being developed, pose a particularly serious microbial contamination problem. Hydrophilic gel contact lenses made of hydroxyethylmethacrylate (HEMA) alone, or copolymerized with various cross-linking and plasticizing agents, can absorb up to 80.0% cold water. These lenses also absorb and complex a variety of environmental low molecular weight organic molecules. These organic molecules may serve as nutrients for microorganisms. Because of the suitable environment for microbial growth which these lenses provide, sterilization is essential.

Chemical sterilization of HEMA lenses with conventional sterilizing solutions has presented serious problems. HEMA lenses complex with most of the conventional preservatives, including benzalkonium chloride, chlorhexidine gluconate, thimerosal sodium, chlorobutanol and phenylmercuric acetate. The possibility of ensuing corneal chemical burns with lenses treated with these conventional preservatives has virtually eliminated the use of these well known germicides. Boiling HEMA containing lenses is not an entirely satisfactory method of sterilization since any ocular mucoid material inadequately removed prior to boiling is denatured within the lens matrix. This leads to loss of lens clarity, discomfort, and eventual destruction of the lens. Boiling or autoclaving HEMA lenses is also disadvantageous because it results in a gradual physical change in the lens geometry and porosity.

An aqueous solution particularly suitable for maintaining sterility of prostheses, such as contact lenses, may be prepared by admixing from 1% to about 10% by weight of an aqueous iodophor solution such as the aqueous iodine-iodide salt-polyvinyl alcohol iodophor previously described, with from about 90% to about 99% by weight of the sterile aqueous solution of the present invention. Prostheses such as contact lenses may be treated by contacting them with the iodophor and then adding the sterile aqueous dissipating solution. The available iodine in the iodophor solution acts to sterilize the prostheses and is slowly dissipated by the dissipating solution. After sterilization and dissipation of the available iodine, a solution is provided which will maintain the sterility of the treated prostheses.

A particularly preferred technique for cleaning and sterilizing soft contact lenses involves, after removal of the lenses, cleaning them with a gel cleaning composition, such as that disclosed in copending U.S. application Ser. No. 377,430, filed July 9, 1973 now U.S. Pat. No. 3,954,644, and placing them in a cleaning and storage device, such as the type shown in U.S. Pat. Nos. 3,519,005 and 3,645,284. The lenses are then washed with water and 4 to 6 drops of an iodine-potassium iodide-PVA iodophor are added to the lens container. Six mls. of the preferred dissipating solution of the present invention is added to the container and the container is shaken. In approximately 15 minutes, the solution in the lens container loses its distinctive iodine color. Within 1 or 2 hours (up to a maximum of 6 to 8 hours), all of the iodine will be dissipated from the lenses, and the lenses may be rinsed and reinserted in the eyes. Lens so treated have been found to be sterile.

The invention will be further explained by reference to the following examples. The following examples, which are not limiting, include preferred embodiments of the present invention. In the following examples, unless otherwise specified, all percentages are by weight.

EXAMPLE I

The following (Solution A) is an exemplary iodophor formulation:

| Iodine | 0.1% |
|---|---|
| Potassium Iodide | 0.2% |
| Polyvinylalcohol (Elvanol 5105) | 2.5% |
| Boric Acid | 0.5% |
| Purified Water Q.S. to make | 100.0% |

The above formulation may be prepared by dissolving the boric acid in about 85.0% of the total water content. The polyvinyl alcohol is dissolved in the boric acid solution with the aid of heat and agitation and the resultant solution allowed to cool. The iodine and potassium iodide are dissolved in 5 to 10% by weight of the total water content and added to the cooled polyvinyl alcohol-boric acid solution. The pH is then adjusted and the remaining water added.

A second solution (Solution B) of the following formulation was prepared:

| Sorbic Acid | 0.1% |
|---|---|
| Trisodium Edetate | 0.1% |
| Sodium Choride | 0.75% |
| Potassium Chloride | 0.20% |
| 5% Sodium Hydroxide Solution to adjust pH to | 7.4% |
| Purified Water Q.S. to make | 100.0% |

The sterility of Solution B was insured by heating.

Eight different hydrophilic soft gel lenses, one pair of flexible silicone lenses, and two pairs of conventional polymethylmethacrylate lenses supplied by contact lens manufacturers were placed in the transfer unit portion of contact lens cleaning and storage devices of the types shown in U.S. Pat. Nos. 3,519,005 and 3,645,284. Four mls. of Solution B (the sterile preservative dissipating solution) were added to each device. From 3 to 6 drops of Solution A (the concentrated disinfectant solution) were added to each device and the test lenses were submerged in the solution for disinfection. Some of the lenses became yellow initially due to their ability to concentrate the available iodine. In these instances, lower levels (from 3 to 4 drops) of the Solution A minimize the initial uptake of iodine. In all instances, the iodine is dissipated from the resulting solution in 1 to 6 hours. At the end of this time, there were no visible or measurable adverse effects on any of the representative lenses in the study. The study was repeated numerous times with basically the same results.

Representative prescription contact lenses were fitted on rabbit corneas after exposure of varying times (1 minute to 8 hours) to mixtures of solutions of A and B in ratio set forth above. There were no adverse effects. Solution A was instilled directly into rabbit eyes with no apparent adverse effects.

Representative lenses were purposely contaminated with actively growing cultures of staphyloccocus aureus, streptoccocus pyogenes, escherichia coli, pseudomonas aeurginosa and candida albicans prior to exposure to mixtures of Solutions A and B described above for varying periods of time. As little as 3 drops of Solution A added to Solution B (resulting concentration of available iodine equivalent to about 0.003% by weight) produced complete kill in 30 minutes.

Representative soft hydrophilic gel, conventional polymethylmethacrylate, and silicone lenses fitted to human corneas were treated with Solutions A and B yielding initial available iodine concentrations ranging from 0.003% to 0.01% for time intervals ranging from 2 hours to 12 hours. These lenses were subsequently worn by human volunteers without any apparent adverse effects.

EXAMPLE II

The following iodophor solution (Solution C) was prepared:

| | |
|---|---|
| Iodine | 0.1% |
| Potassium Iodide | 0.3% |
| Polyvinylalcohol (Elvanol 5105) | 2.0% |
| Sodium Chloride | 0.7% |
| Purified Water Q.S. to make | 100.0% |

The solution was prepared following the procedure set forth in Example I, except for the omission of the step of dissolving boric acid prior to dissolving the polyvinyl alcohol. Subsequently, hydrochloric acid was added to the solution to adjust the pH to 4.

A second solution (Solution D) of the following formulation was also prepared:

| | |
|---|---|
| Sorbic Acid | 0.1% |
| Disodium Edetate | 0.1% |
| Sodium Chloride | 0.6% |
| Potassium Chloride | 0.2% |
| Sodium Borate | 0.2% |
| Purified Water Q.S. to make | 100.0% |

Suspensions of the test organisms shown in Table 1 were prepared and adjusted to contain a final population of approximately $1 \times 10^5$ cells per ml. of final fluid volume. Seven drops of Solution C were added to sterile contact lens carrying cases and hydrophilic soft gel lenses were placed in the cases. One-tenth ml. of inoculum was then added to the cases. Seven ml. of Solution D were added to the cases which were closed and shaken vigorously through an arc of one foot for 60 seconds. Inoculated units were placed on a workbench in normal room light for 60 minutes. After the holding period most of the iodine color had disappeared from the solution. A viability control was inoculated and treated in the same manner except that physiological saline was used instead of Solutions C and D.

Tests with each organism were carried out in triplicate. After the 60 minute exposure period the entire contents of the carrying cases were aseptically transferred to 40 ml. Tryptic Soy Broth (TSB) or Fluid Thioglycolate Broth (THIO) containing neutralizers and incubated at the optimum growth temperature of the test organism for 14 days. Sterile blood was added to recovery media utilized for culturing N. gonorrhea, Haemophilus influenzae, Moraxella sp., and β-hemolytic streptococci. These cultures were subcultured to blood agar media after 1, 2, 7 and 14 days incubation to verify status of organism viability since growth in the broth medium was obscured by the added blood.

The results of these tests are summarized in Table 1. As is apparent, Solution C in Solution D is very effective for disinfecting soft contact lenses. Bacterial spores survived exposure. Survivors were recovered from units inoculated with vegetative cells of the spore forming bacteria; however, survivors from these suspensions represent spores that were present in the preparation. The remaining test organisms could not be recovered after treatment.

Table 1

| Disinfecting Efficacy of Solution A in Solution B | | | | | | |
|---|---|---|---|---|---|---|
| | | | Days After Inoculation When Growth First Observed | | | |
| | INOCULUM | | Test No. | | | POSITIVE |
| TEST ORGANISM | CELLS/ML (×10⁵) | MEDIUM | 1 | 2 | 3 | CONTROL |
| Bacillus cereus (Veg.) | 2.8 | TH10² | 2 | NG¹ | NG | 1 |
| Bacillus cereus (Spores) | 1.7 | TSB³ | 1 | 1 | 1 | 1 |
| Bacillus subtilis (Veg.) | 2.57 | TH10 | 2 | 2 | 2 | 1 |
| Bacillus subtilis (Spores) | 2.8 | TSB | 1 | 1 | 1 | 1 |
| Escherichia coli | 1.8 | TH10 | NG | NG | NG | 1 |
| Proteus mirabilis | 1.41 | TH10 | NG | NG | NG | 1 |
| Proteus vulgaris | 1.8 | TH10 | NG | NG | NG | 1 |
| Pseudomonas aeroginosa | 1.5 | TH10 | NG | NG | NG | 1 |
| Serratia marcescens | 2.2 | TH10 | NG | NG | NG | 1 |
| Staphylococcus aureus | 3.28 | TH10 | NG | NG | NG | |
| Staphylococcus epidermidis | 6.57 | TH10 | NG | NG | NG | 1 |
| Aspergillus niger | 2.14 | TSB | NG | NG | NG | 5 |
| Fusarium solani | 3.28 | TSB | NG | NG | NG | 3 |
| Candida albicans | 6.92 | TSB | NG | NG | NG | 1 |
| Candida parapsilosis | 3.57 | TSB | NG | NG | NG | 1 |
| Neisseria gonorrhea | 3.93 | TH10/B⁴ | NG | NG | NG | 2 |
| Propionibacterium acnes | 1.27 | TH10 | NG | NG | NG | 3 |

Table 1-continued

Disinfecting Efficacy of Solution A in Solution B

| TEST ORGANISM | INOCULUM CELLS/ML (×10[5]) | MEDIUM | Days After Inoculation When Growth First Observed Test No. 1 | 2 | 3 | POSITIVE CONTROL |
|---|---|---|---|---|---|---|
| *Haemophilus influenzae* | 1.85 | TH10/B | NG | NG | NG | 2 |
| *Moraxella species* | 3.42 | TH10/B | NG | NG | NG | 1 |
| *β-hemolytic streptococcus* | 1.53 | TH10/B | NG | NG | NG | 2 |

[1]NG = No growth after 14 days incubation.
[2]TH10 = Fluid Thioglycolate Broth.
[3]TSB = Tryptic Soy Broth.
[4]TH10/B = Fluid Thioglycolate Broth supplemented with blood.

The invention in its broader aspects is not limited to the specific details shown and described and departures may be made from such details without departing from the principles of the invention and without sacrificing its chief advantages.

What is claimed is:

1. A sterile aqueous solution suitable for dissipating available iodine contained in an iodophor at a controlled rate, consisting essentially of:
   a. from about 0.01% to about 5% by weight sorbic acid or a soluble salt thereof; and
   b. from about 0.01% to about 5% by weight ethylenediaminetetraacetic acid or a soluble salt thereof.

2. The solution of claim 1 which additonally contains from about 0.1% to about 2% of an ammonium, alkali metal or alkaline earth metal salt of a boron oxyacid.

3. The solution of claim 2 wherein said salt is sodium borate.

4. The solution of claim 2 which additionally contains up to about 2% of a water soluble alkali metal or alkaline earth metal salt of a mineral acid.

5. A sterile aqueous solution comprising an admixture of
   a. from about 1% to about 10% by weight of an aqueous iodophor solution comprising from about 0.00005% to about 10% by weight iodine, from about 0.0001% to about 20% by weight of a water soluble iodide salt or hydriotic acid, and from about 0.001% to about 25% by weight polyvinyl alcohol; and
   b. from about 90% to about 99% by weight of a sterile aqueous solution comprising from about 0.01% to about 5% by weight sorbic acid or a soluble salt thereof; from about 0.01% to about 5% by weight ethylenediaminetetraacetic acid or a soluble salt thereof; and about 0.1% to about 2% of an ammonium, alkali metal, or alkaline earth metal salt of a boron oxyacid.

6. The aqueous solution of claim 5 in which the pH of said iodophor solution is adjusted to be within the range of about 3 to 8.

7. The process of claim 6 in which said pH is adjusted with an acid selected from the group consisting of $H_3PO_4$, HCl, acetic, $H_2SO_4$, and nitric.

8. The aqueous solution of claim 6 in which said iodophor solution has a pH of less than 7.

9. The aqueous solution of claim 5 in which said iodophor solution contains from about 0.002% to about 5% by weight iodine, about 0.004% to about 10% by weight water soluble iodide salt or hydriotic acid, and from about 0.1% to about 20% by weight polyvinyl alcohol.

10. The aqueous solution of claim 5 in which said iodophor solution includes a water soluble iodide salt selected from the group consisting of potassium iodide and sodium iodide.

11. The aqueous solution of claim 5 in which the tonicity of said iodophor solution is adjusted to the equivalent of a 0.1% to a 5% aqueous sodium chloride solution.

12. The aqueous solution of claim 11 in which the tonicity is adjusted by the addition of appropriate amounts of alkali metal and alkaline earth metal salts of mineral acids.

13. The aqueous solution of claim 5 having a viscosity range within the range of from 1.1 to 10,000 cp at 20° C.

14. The aqueous solution of claim 5 which has a surface tension within the range of from about 40 to about 72 dynes/cm$^2$.

15. A method of dissipating available iodine contained in an iodophor comprising adding to said iodophor, in an amount of from 1 to 1000 parts by weight per part of available iodine in said iodophor, the aqueous solution of claim 1.

16. A method of dissipating available iodine contained in an iodophor comprising adding to said iodophor, in an amount of from 1 to 1000 parts by weight per part of available iodine in said iodophor, the aqueous solution of claim 2.

17. A method of sterilizing contact lenses comprising:
   a. contacting said lens with an aqueous antiseptic iodophor solution comprising from about 0.00005% to about 10% by weight iodine, from about 0.0001% to about 20% by weight of a water soluble iodide salt or hydriotic acid, and from about 0.001% to about 25% by weight polyvinyl alcohol; and
   b. dissipating available iodine contained in said iodophor by adding to said aqueous iodophor solution in an amount of from about 90% to about 99% by weight based on the total weight of the combined solutions, an antioxidant having a redox potential adequate to convert $I_2$ to $2I^-$, which antioxidant comprises an aqueous dissipating solution comprising from about 0.01% to about 5% by weight sorbic acid or a soluble salt thereof; from about 0.01% to about 5% by weight ethylenediaminetetraacetic acid or a soluble salt thereof; and about 0.1% to about 2% of an ammonium, alkali metal, or alkaline earth metal salt of a boron oxyacid.

18. The method of claim 17 in which said aqueous antiseptic iodophor solution has a pH within the range of about 3 to 7.

19. The method of claim 17 in which said lens is a hydrophilic gel lens.

* * * * *